United States Patent [19]

Burmer

[11] Patent Number: 5,726,022
[45] Date of Patent: Mar. 10, 1998

[54] SUBTRACTIVE HYBRIDIZATION AND CAPTURE METHODS AND KITS FOR DIFFERENTIAL ISOLATION OF NUCLEIC ACIDS INCLUDING DISEASE-ASSOCIATED SEQUENCES

[75] Inventor: Glenna C. Burmer, Seattle, Wash.

[73] Assignee: LifeSpan BioSciences, Inc., Seattle, Wash.

[21] Appl. No.: 781,118

[22] Filed: Jan. 9, 1997

Related U.S. Application Data

[60] Provisional application No. 60/010,207, Jan. 18, 1996.

[51] Int. Cl.$^6$ .............................. C12Q 1/68; C12P 19/34; C07H 21/04
[52] U.S. Cl. ........................ 435/6; 435/91.2; 536/24.2; 536/24.33; 935/8; 935/78
[58] Field of Search ...................... 435/6, 91.2, 810; 536/24.2, 24.33; 935/78, 8

[56] References Cited

U.S. PATENT DOCUMENTS

| | | | |
|---|---|---|---|
| 5,436,142 | 7/1995 | Wigler et al. | 435/91.2 |
| 5,501,964 | 3/1996 | Wigler et al. | 435/91.2 |

FOREIGN PATENT DOCUMENTS 8912695 12/1989 WIPO.

OTHER PUBLICATIONS

Lisitsyn et al., *Science* 259:946 (1993).

*Primary Examiner*—Carla J. Myers
*Attorney, Agent, or Firm*—Townsend and Townsend and Crew LLP

[57] ABSTRACT

The invention disclosed here allows for the differential isolation of nucleic acid sequences that are present in one nucleic acid population and not in another. The method is based upon using restriction endonucleases to digest two populations of nucleic acid, preferably cDNAs, preferably ligating different sets of adaptors to each of the two nucleic acid populations, followed by hybridization, restriction digestion and isolation of the desired molecules. The unique aspects of this invention include the use of a restriction enzyme to isolate the target duplex DNA molecule from a hybridization mixture. Certain embodiments of the invention include the direct or indirect incorporation of a capture molecule or ligand (e.g., biotin, dioxigenin) within the amplified nucleic acid fragments, which allows for a system in which molecules can be rescued from both the captured population as well as the effluent or otherwise uncaptured population.

16 Claims, No Drawings

SUBTRACTIVE HYBRIDIZATION AND CAPTURE METHODS AND KITS FOR DIFFERENTIAL ISOLATION OF NUCLEIC ACIDS INCLUDING DISEASE-ASSOCIATED SEQUENCES

This application claims the benefit of U.S. Provisional Application No. 60/010,207, filed Jan. 18, 1996, the disclosure of which is incorporated by reference.

FIELD OF THE INVENTION

This invention relates to the field of nucleic acid analysis and differentiation.

BACKGROUND OF THE INVENTION

The ability to identify and target nucleic acid sequences which appear in one nucleic acid sample and not in another is of intense interest in the field of molecular biology. The identification of novel nucleic acid sequences can provide valuable clues as to genetic bases for disease, inherited dominant and recessive traits, genetic alterations which give rise to diseases such as cancer, determining species similarities and differences, genotyping, and taxonomic classification. Such technology has applications thus in diagnostics, medicine and health, forensics, taxonomic classification and the like.

Various comparative nucleic acid techniques are available to analyze differences in nucleic acid populations. One widely known technique is referred to as "representational difference analysis" (RDA); see, for example, U.S. Pat. No. 5,436,142 and Lisitsyn et al., *Science* 259:946 (1993). RDA is a subtractive hybridization method that uses restriction digestion of genomic DNA, followed by amplification and selection methods to isolate molecules that are present in one population but are lacking in a second nucleic acid sample. This method however requires multiple steps, numerous costly reagents and several weeks of time in the laboratory to obtain results.

Genomic analysis, particularly at the human level, is highly complex and involves the analysis of tremendous amounts of nucleic acid. Processes which can selectively, simply and quickly isolate disease-associated sequences from complex nucleic acid samples will enable the science of molecular biology to uncover the keys to the genome and to disease.

SUMMARY OF THE INVENTION

The invention disclosed here allows for the differential isolation of nucleic acid sequences that are present in one nucleic acid population and not in another. The method is based upon using restriction endonucleases to digest two populations of nucleic acid, preferably cDNAs, ligating different sets of adaptors to each of the two nucleic acid populations, followed by hybridization, restriction digestion and isolation of the desired molecules. The unique aspects of this invention include the use of a restriction enzyme to isolate the target duplex DNA molecule from a hybridization mixture. Certain embodiments of the invention include the direct or indirect incorporation of a capture molecule or ligand (e.g., biotin, digoxigenin) within the amplified nucleic acid fragments, which allows molecules to be rescued from both the captured population as well as the effluent or otherwise uncaptured population.

The methods described here are applicable to a wide variety of situations. In determining the presence or absence of particular DNA sequences, particularly associated with recessive or dominant traits, one can compare two related sources of DNA to determine whether they share the particular sequence, where the sequence may be a coding or non-coding sequence, but will be inherited in association with the DNA sequence associated with the trait. One can use the subject methods in forensic medicine, to establish similarities between the DNA from two sources, where one is interested in the degree of relationship between the two sources. The subject methods can also be applied in the study of diseases, where one can investigate the presence of a sequence associated with infection or cause, such as a viral sequence which may or may not be integrated into the genome. One may also use samples from a non-infectious disease source and compare it with a source without the disease to determine if there is a genetic basis, to identify genetic rearrangements, and for the identification of polymorphisms. Further, differences can be elucidated in species of interest to aid in taxonomic classification or even to determine possible contamination in nucleic acid samples of interest.

DETAILED DESCRIPTION

The methods and kits of this invention provide for simple and relatively inexpensive means to determine similarities or differences between two nucleic acid populations. Basically, the methods provide for:

(1) Fragmentation of sample nucleic acid by restriction digestion. The fragmentation of the nucleic acid in which unique sequences are suspected (the "first nucleic acid sample") and the restriction digestion of the nucleic acid to which the first nucleic acid is to be compared (the "second nucleic acid sample"). Preferably the nucleic acid samples are cDNA samples derived from RNA. The first and second nucleic acid samples are subjected to a restriction endonuclease to produce fragments ("first and second nucleic acid sample fragments", respectively).

(2) Ligation of Adaptors. Adaptors with a restriction site are ligated to the first nucleic acid sample fragments and adaptors with a second and preferably a different restriction site are ligated to the second nucleic acid sample fragments. The adaptors may optionally contain a ligand binding end (defined below).

(3) Optional Fragment Amplification. If the first and second nucleic acid sample fragments are amplified, they are amplified with primers containing a ligand binding end and a sequence complementary to the adaptors.

(4) Hybridization of First and Second Nucleic Acid Fragments. The first and second nucleic acid fragments are combined under hybridization conditions.

(5) Isolation of Target Nucleic Acid. Double-stranded nucleic acid fragments in which both strands are first nucleic acid fragments are isolated.

The last step is preferably done by first removing the adaptors by restriction digestion and then capturing the molecules which still contain the ligand binding end. The molecules which are not captured may then be isolated and amplified. The method will be described in more detail below.

A. Fragmentation of Sample Nucleic Acid.

For the purposes of this invention, two or more sources of nucleic acid are used from which the test samples are to be derived for comparison purposes. The sources of nucleic acid may be any sources of nucleic acid in which one is interested in comparing for differences. The sources may be eukaryotic, prokaryotic, invertebrate, vertebrate, mammalian, non-mammalian, plant and others.

The methods described here are particularly well-suited to the use of cDNA, which is preferred when complex genomes are of interest. RNA may be isolated by any known means as a subset of the genomic nucleic acid and subsequent synthesis of cDNA. The use of RNA provides a unique source as it represents an initial fragmentation of the genome.

It is also desirable to use cDNA as the first nucleic acid sample in assays in which cDNA or RNA is used as the second nucleic acid sample to prevent the isolation of products that are derived from intronic genomic sequences. For any of the analysis methods described here, it will be understood that RNA viruses, novel mRNAs expressed in cancers and other RNA of interest such as RNA used as a representation of a genome of interest can be detected by first obtaining corresponding cDNA by any method known in the art such as by using reverse transcriptase. See, for example, Innis et al., *PCR Protocols, infra* and Ehrlich, ed., *PCR Technology,* W. H. Freeman and Company, N.Y. (1991), incorporated by reference herein.

If genomic DNA is to be the source, it is isolated, freed of protein, and then substantially completely digested with at least one restriction nuclease. Not all restriction endonucleases will be equivalent in the ease with which target DNA may be identified. Therefore, in each case it may be desirable to use a plurality of restriction endonucleases in separate determinations, not only to ensure that one obtains target DNA within a reasonable number of cycles, but also to increase the number of target DNA sequences that may be obtained. Alternatively and conveniently, though, as described above, RNA may be the source of nucleic acid, and cDNA is synthesized for testing, representing a subset of a genomic sample. Normally the first and second nucleic acid samples will be those which are expected to have substantially similar nucleic acid sequences.

Whatever the source, the first and second nucleic acid samples are separately subjected to at least one restriction endonuclease. The restriction endonuclease may provide for blunt ends or staggered (sticky) ends, usually staggered ends. It is preferred that both first and second nucleic acid samples are subjected to the same restriction endonuclease and that such endonuclease is one which recognizes and cuts at a four base site. For the subsequent steps it is further preferred that such restriction endonuclease be one which recognizes a four base sequence found within a longer six base or eight base sequence recognized by a restriction endonuclease. Almost 1500 restriction endonucleases are now known and at least 150 are commercially available. Complete lists plus details of restriction sites and reaction conditions are published, for example in Brown, T. A. *Molecular Biology Labfax,* BIOS, Oxford (1991).

B. Ligation of Adaptors.

Once the first and second nucleic acid samples have been separately fragmented to produce first and second nucleic acid sample fragments, double-stranded oligonucleotide adaptors are ligated onto the ends of each of the strands of the fragments. The adaptor will usually be staggered at both ends, with one strand being longer than the other. The adaptors will generally serve to provide the sequence complementary to a primer to be used when a subsequent amplification step is employed. Thus, typically one end of the adaptor will be double-stranded and have one end complementary to the ends of the double-stranded nucleic acid fragments from the digestion, sometimes referred to herein as the proximal end of the adaptor. Each adaptor will preferably further contain a restriction site located distal to the proximal end.

The restriction site in the adaptor is preferably one which has a six or eight base consensus sequence, and most preferably is such a one that further contains a 3' sequence that ends in a four base consensus sequence that has ends that are complementary to the same ends that are created by the six or eight base cutter that is adjacent and external to it. Examples of such restriction endonucleases include, but are not limited to, DpnII ('GATC); BglII (A'GATCT); BamHI (G'GATCC); Tsp509I ('AATT), EcoRI (G'AATTC) and PacI (TT'AATTAA).

It is preferred for the purposes of the methods of this invention that the adaptors used for the first nucleic acid sample fragments contain a restriction site which is different than the one used in the adaptors for the second nucleic acid sample fragments. The adaptor may further optionally contain a ligand binding end. A ligand binding end is particularly important if the fragments will not be amplified. It is preferred that the adaptor have one strand longer than the other to serve as a complement to primers if the fragments are to be amplified.

In one embodiment, only the first nucleic acid sample fragments will contain adaptors having a restriction site. The second nucleic acid sample fragments do not necessarily need to have adaptors or a primer used for amplification with a restriction site. If this embodiment is employed, the adaptors and/or primers for the second nucleic acid sample fragments will have a ligand binding moiety to enable capture of the second nucleic acid sample fragments.

Further, in another embodiment, it is possible to ligate the same adaptors onto nucleic acid of the first nucleic acid sample and the second nucleic acid sample if different primers are subsequently used to amplify the two sample populations so long as a restriction endonuclease site is encoded within the primers used to amplify the first nucleic acid sample fragments.

Additionally, the adaptor ligated onto the first nucleic acid sample fragments may have "non-nested" restriction endonuclease sites; e.g. 5'EcoRI—GATC3', where the EcoRI site is external to an initial DpnII digestion site. This protocol is less preferred, however, because when the EcoRI site is subsequently targeted by the restriction endonuclease in order to release the homoduplex from its biotinylated adaptors, approximately 1/16 of the cDNA molecules may contain an internal EcoRI site.

C. Optional Amplification of First and Second Nucleic Acid Fragments.

The first and second nucleic acid fragments may be separately amplified to enhance the assay, preferably by the polymerase chain reaction or other methods discussed in general below, using primers containing a sequence complementary to the respective adaptors and a ligand binding end.

Thus, the second nucleic acid sample fragments and the first nucleic acid sample fragments may be amplified separately by adding appropriate primers complementary to the adaptors using the polymerase chain reaction (PCR), typically for about 10–35 cycles, more typically about 20 cycles, depending upon the initial concentration of second or first nucleic acid sample fragments being amplified. For a general overview of PCR, see *PCR Protocols: A Guide to Methods and Applications* (Innis, M.; Gelfand, D.; Sninsky, J. and White, T.; eds.), Academic Press, San Diego (1990), and U.S. Pat. Nos. 4,683,195 and 4,683,202, all incorporated herein by reference. In the methods described, here, the adaptors do not need to be removed.

D. Hybridization of First and Second Nucleic Acid Fragments.

The amplified first and second nucleic acid sample fragments are combined under hybridization conditions such that the fragments hybridize together creating essentially several possible complexes: first nucleic acid/second nucleic acid matches, second nucleic acid/second nucleic acid matches, and first nucleic acid/first nucleic acid matches. It is preferred that the second nucleic acid fragments are present in excess of the first nucleic acid sample fragments to increase the probability that the first nucleic acid/first nucleic acid complexes are representative of nucleic acid not found in the second nucleic acid sample.

Second nucleic acid sample fragments will then be combined with the adaptor-ligated first nucleic acid fragments, with the second nucleic acid sample fragments present in excess, usually at least 5-fold excess and less than 500-fold excess, preferably about 100-fold excess for the first cycle of hybridization. Hybridization will be allowed to proceed at high stringency temperatures, usually about 60°–70° C. Various buffers and salt concentrations may be used to adjust for the desired stringency as will be appreciated by those in the art.

E. Isolation of First Nucleic Acid/First Nucleic Acid Complexes.

The first nucleic acid/first nucleic acid complexes present in the combined first and second nucleic acid solution can be readily separated from the other complexes depending upon the ligand used. Most conveniently, all of the combined fragments will be subjected to a restriction enzyme which recognizes the site in the first nucleic acid sample adaptors which will effectively remove the ligand binding end from the first nucleic acid/first nucleic acid molecules and not from the others. Thus, by capture technology which will attract the ligand binding end of the second nucleic acid/first nucleic acid complexes, one can readily separate out the first nucleic acid/first nucleic acid complexes. The first nucleic acid/first nucleic acid complexes may be further amplified and isolated, by, for example, ligating new adaptors onto the ends of the molecules and amplifying by PCR.

It may be of interest to carry out the process more than once, where different restriction endonucleases are used. Different fragments may be obtained and result in additional information.

Any resulting unique first nucleic acid sequences (i.e. those not found in the second nucleic acid sample) can be used as probes to identify sites in the first nucleic acid sample which differ from the second nucleic acid source. For this purpose they may be labeled in a variety of ways. Desirably in order to obtain substantially homogeneous compositions of each of the first nucleic acid sample sequences, the first nucleic acid sample sequences may be cloned by inserting into an appropriate cloning vector for cloning in a prokaryotic host. If desired, the cloned DNA may be sequenced to determine the nature of the target DNA. Alternatively, the cloned DNA may be labeled and used as probes to identify fragments in libraries carrying the target DNA. The target DNA may be used to identify the differences which may be present between the two sources of nucleic acid.

The resulting target DNA will be greatly enriched. It may be used as probes to identify sites on the first nucleic acid sample sequences which differ from the second nucleic acid. The target nucleic acid may be sequenced directly by PCR or it may be cloned by inserting it in a cloning vector for cloning into a host cell. The cloned DNA can be sequenced to determine the nature of the target DNA through the use of dot blotting or other procedure. It may also be labeled and used as probes to identify fragments in libraries carrying the target DNA. Sequences can be identified and cloned for sequencing. Comparative searches with sequences described in accessible libraries such as Genbank (National Center for Biotechnology Information, Natl. Library of Medicine, National Institutes of Health, 8600 Rockville Pike, Bethesda, Md. 20894); Protein Identification Resource (PIR, Natl. Biomedical Research Foundation, 3900 Reservoir Road NW, Washington, D.C. 20007; EMBL, European Molecular Biology Laboratory, Heidelberg, Germany) can aid in identifying the sequence.

Other Definitions and General Techniques

The term "ligand" or "ligand binding end" refers to a component which may directly or indirectly be detected or captured by another component, the "anti-ligand" which permits the physical or chemical separation of compositions bearing the ligand from those which do not. The ligand will be attracted to an anti-ligand molecule such that molecules which do not bear the ligand will not be captured or otherwise attracted to the anti-ligand. The ligand will need to be one which may be attached directly or indirectly to nucleic acid sequences. Examples of direct ligand binding include the use of biotin labeled nucleotides or the use of digoxigenin. These molecules can be used as the ligand binding component. They can be readily captured by their anti-ligand, e.g. avidin or streptavidin in the case of biotin and an anti-digoxigenin antibody, bound on a suitable substrate. (These reagents are all readily available, see Clontech Laboratories, Inc., Palo Alto, Calif. for digoxigenin reagents, for example.) Molecules which do not bind the anti-ligand can be collected and captured, by for example passing them through a streptavidin column. This direct capture method is preferred as it is likely to be the simplest, least costly and most efficient of the capture technologies available.

Nevertheless other methods may be used as well so long as they accomplish a similar purpose. The ligand could alternatively be a specific nucleic acid sequence with the anti-ligand being the complement of the sequence or an antibody specific for the sequence. The ligand could include labeled molecules which may be manipulated on a substrate so that they are physically or chemically separated from non-ligand bearing molecules. Alternatively, the ligand molecule can have affinity for an anti-ligand molecule which is labeled or inherently detectable. These compositions can be further detectable by spectroscopic, photochemical, biochemical, immunochemical, or chemical means. For example, useful nucleic acid labels may include enzymes (e.g., LacZ, CAT, horse radish peroxidase, alkaline phosphatase and others, commonly used as detectable enzymes, either as marker gene products or in an ELISA), nucleic acid intercalators (e.g., ethidium bromide) and colorimetric labels such as colloidal gold or colored glass or plastic (e.g. polystyrene, polypropylene, latex, etc.) beads, substrates, cofactors, inhibitors, fluorescent moieties (e.g., fluorescein and its derivatives, Texas red, rhodamine and its derivatives, dansyl, umbelliferone and the like), chemiluminescent moieties (e.g. luciferin and 2,3-dihydrophthalazinediones), magnetic particles, and the like. Labeling agents optionally include e.g., monoclonal antibodies, polyclonal antibodies, proteins, or other polymers such as affinity matrices, carbohydrates or lipids, fluorescent dyes, electron-dense reagents, enzymes (e.g., as commonly used in an ELISA), or haptens and proteins for which antisera or monoclonal antibodies are available. A wide variety of labels suitable for labeling nucleic acids and conjugation techniques are known and are reported extensively in both the scientific and patent literature, and are generally applicable to the present invention for the labeling of nucleic acids, or amplified nucleic acids for detection and isolation by the methods of the invention. The choice of label depending on the sensitivity required, ease of conjugation of the compound, stability requirements, available instrumentation, and disposal provisions. Separation and detection of nucleic acids proceeds by any known method, including immunoblotting, tracking of radioactive or bioluminescent markers, Southern blotting, northern blotting, southwestern blotting, northwestern blotting, or other methods which track a molecule based upon size, charge or affinity.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence, e.g., by microscopy, visual inspection, via photographic film, by the use of electronic detectors such as charge coupled devices (CCDs) or photomultipliers and the like.

Similarly, enzymatic labels may be detected by providing appropriate substrates for the enzyme and detecting the resulting reaction product. Finally, simple colorimetric labels are often detected simply by observing the color associated with the label. Thus, in various dipstick assays, conjugated gold often appears pink, while various conjugated beads appear the color of the bead.

Substrates to be used as an environment for the capture and separation of the ligand bound molecules from those without ligand depend on the ligand being used and the desired format. For instance, the solid surface is optionally paper, or a membrane (e.g., nitrocellulose), a microtiter dish (e.g., PVC, polypropylene, or polystyrene), a test tube (glass or plastic), a dipstick (e.g. glass, PVC, polypropylene, polystyrene, latex, and the like), a microcentrifuge tube, or a glass, silica, plastic, metallic or polymer bead or other substrate as described herein. The desired anti-ligand may be covalently bound, or noncovalently attached to the substrate through nonspecific bonding.

A wide variety of organic and inorganic polymers, both natural and synthetic may be employed as the material for the solid surface. Illustrative polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials which are appropriate depending on the assay include paper, glasses, ceramics, metals, metalloids, semiconductive materials, cements and the like. In addition, substances that form gels, such as proteins (e.g., gelatins), lipopolysaccharides, silicates, agarose and polyacrylamides can be used. Polymers which form several aqueous phases, such as dextrans, polyalkylene glycols or surfactants, such as phospholipids, long chain (12–24 carbon atoms) alkyl ammonium salts and the like are also suitable. Where the solid surface is porous, various pore sizes may be employed depending upon the nature of the system.

In preparing the surface, a plurality of different materials are optionally employed, e.g., as laminates, to obtain various properties. For example, protein coatings, such as gelatin can be used to avoid non specific binding, simplify covalent conjugation, enhance signal detection or the like. If covalent bonding between a compound and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. In addition to covalent bonding, various methods for noncovalently binding an anti-ligand component can be used. For additional information regarding suitable ligand-anti-ligand and labeling technology as it relates to nucleic acids, see, for example, *Essential Molecular Biology*, ed. T. A. Brown IRL Press (1993); *In Situ Hybridization Protocols*, ed. K. H. Andy Choo, Humana Press (1994).

By a nucleic acid sequence "homologous to" or "complementary to", it is meant a nucleic acid that hybridizes, duplexes or binds only to DNA sequences encoding one protein or portions thereof. A DNA sequence which is homologous to a target sequence can include sequences which are shorter or longer than the target sequence so long as they meet the functional test set forth. Hybridization conditions are specified along with the source of the DNA. Typically the hybridization is done in a Southern blot protocol using a 0.2XSSC, 0.1% SDS, 65° C. wash. The term "SSC" refers to a citrate-saline solution of 0.15M sodium chloride and 20 mM sodium citrate. Solutions are often expressed as multiples or fractions of this concentration. For example, 6XSSC refers to a solution having a sodium chloride and sodium citrate concentration of 6 times this amount or 0.9M sodium chloride and 120 mM sodium citrate. 0.2XSSC refers to a solution 0.2 times the SSC concentration or 0.03M sodium chloride and 4 mM sodium citrate.

Accepted means for conducting hybridization assays are known and general overviews of the technology can be had from a review of: *Nucleic Acid Hybridization: A Practical Approach*, Ed. Hames, B. D. and Higgins, S. J., IRL Press, 1985; *Hybridization of Nucleic Acids Immobilized on Solid Supports*, Meinkoth, J. and Wahl, G.; *Analytical Biochemistry*, Bol 238, 267–284, 1984 and Innis et al., *PCR Protocols, supra*, all of which are incorporated by reference herein.

Nucleic acids of interest in the present invention may be cloned or amplified, or any of the nucleic acid fragments may be amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB). A wide variety of cloning and in vitro amplification methodologies are well-known to persons of skill. Examples of these techniques and instructions sufficient to direct persons of skill through many cloning exercises are found in Berger and Kimmel, *Guide to Molecular Cloning Techniques, Methods in Enzymology* 152 Academic Press, Inc., San Diego, Calif. (Berger); Sambrook et al. (1989) *Molecular Cloning—A Laboratory Manual* (2nd ed.) Vol. 1–3, Cold Spring Harbor Laboratory, Cold Spring Harbor Press, N.Y., (Sambrook et al.); *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel); Cashion et al., U.S. Pat. No. 5,017,478; and Carr, European Patent No. 0,246,864. Examples of techniques sufficient to direct persons of skill through in vitro amplification methods are found in Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36–47; *The Journal Of NIH Research* (1991) 3, 81–94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem* 35, 1826; Landegren et al., (1988) *Science* 241, 1077–1080; Van Brunt (1990) *Biotechnology* 8, 291–294; Wu and Wallace, (1989) *Gene* 4, 560; and Barringer et al. (1990) *Gene* 89, 117.

The term "identical" in the context of two nucleic acid sequences refers to the residues in the two sequences which are the same when aligned for maximum correspondence. Sequences which are not identical are "different."

F. Kits

Further contemplated are kits for the assays described here. Combinations of reagents useful in the methods set out above can be packaged together with instructions for using them in the described method. In particular, kits containing a separate container for first nucleic acid sample adaptors and for second nucleic acid sample adaptors can be prepared. Preferably such kits will also contain instructions for the subtractive capture methods. Alternatively the kits can contain separate containers for primers to amplify the first nucleic acid sample fragments and primers to amplify the second nucleic acid sample fragments as described above. Further, the kits could contain separate containers of first nucleic acid sample primers, second nucleic acid sample primers, first nucleic acid sample adaptors and second nucleic acid sample adaptors, all as described above.

Population A:
B-NNNGGATCCGATCTTTTGATCGGATCCNNN-3' (SEQ ID NO:1)
3'-NNNCCTAGGCTAGAAAACTAGCCTAGGNNN-B (SEQ ID NO:2)

B-NNNGGATCCGATCGGGGGATCGGATCCNNN-3' (SEQ ID NO:3)
3'-NNNCCTAGGCTAGCCCCCTAGCCTAGGNNN-B (SEQ ID NO:4)

B-NNNGGATCCGATCXXXXGATCGGATCCNNN-3' (SEQ ID NO:5)
3'-NNNCCTAGGCTAGXXXXCTAGCCTAGGNNN-B (SEQ ID NO:5)

All of the literature and patent references cited herein provide additional background and general guidance and are incorporated by reference herein.

G. Examples

The following examples are all illustrative only and are not to be construed as a limitation of the invention. Those of skill in the art will readily recognize a variety of noncritical parameters which can be changed or modified to yield essentially similar results.

One embodiment of the methods described here is set forth below. In adaptor set A, the biotin (B) groups are adjacent to a BamH1 site, and in adaptor set B, they are adjacent to the BglII site. The combination of a capture moiety with a particular 6 or greater cutter restriction enzyme is entirely discretionary, however the capture group is located externally relative to the 6-cutter site. The six or eight cutters that are most suitable are those that have two characteristics: they are not blunt end cutters, and they contain within their recognition sequence a 4 base restriction site. Examples of such suitable combinations are DpnII ('GATC) and BglII (A'GATCT) or BamHI (G'GATCC), or alternatively Tsp509I ('AATT) and EcoRI (G'AATTC) or PacI (TT'AATTAA).

Example 1

Isolation of sequences from nucleic acid population A (i.e., sequence GATCXXXX) that are not present in nucleic acid population B using physical capture. After cDNA is made from RNA by routine methods, the DNA from each population is digested with the four cutter DpnII:

(a) Digestion with DpnII

| Population A: | Population B: |
|---|---|
| 5-GATCTTTT-3 | 5-GATCTTTT-3 |
| 3-AAAACTAG-5 | 3-AAAACTAG-5 |
| 5-GATCGGGG-3 | 5-GATCGGGG-3 |
| 3-CCCCCTAG-5 | 3-CCCCCTAG-5 |
| 5-GATCXXXX-3 | |
| 3-XXXXCTAG-5 | |

(b) and (c) Ligate adaptors and amplify (adaptors flank the sequence)

Population B:
B-NNNAGATCTGATCTTTTGATCAGATCTNNN-3' (SEQ ID NO:6)
3'-NNNTCTAGACTAGAAAACTAGTCTAGANNN-B (SEQ ID NO:7)

B-NNNAGATCTGATCGGGGGATCAGATCTNNN-3' (SEQ ID NO:8)
3'-NNNTCTAGACTAGCCCCCTAGTCTAGANNN-B (SEQ ID NO:8)

(d) Hybridization with B in excess relative to A produces three types of double-stranded molecules, plus single stranded non-hybridized molecules:

| | |
|---|---|
| B-NNNGGATCCGATCTTTTGATCGGATCCNNN-3' (SEQ ID NO:1)<br>3'-NNNTCTAGACTAGAAAACTAGTCTAGANNN-B (SEQ ID NO:7) | Mismatched A:B Heteroduplexes |
| B-NNNAGATCTGATCGGGGGATCAGATCTNNN-3' (SEQ ID NO:8)<br>3'-NNNTCTAGACTAGCCCCCTAGTCTAGANNN-B (SEQ ID NO:9) | B:B complexes with BglII sites |
| B-NNNGGATCCGATCXXXXGATCGGATCCNNN-3' (SEQ ID NO:5)<br>3'-NNNCCTAGGCTAGXXXXCTAGCCTAGGNNN-B (SEQ ID NO:5) | A:A complexes with BamHI sites |

(e) and (f) Digest all molecules with BamHI, capture with streptavidin column. In this step, only the A:A complex is eluted from the column:

5'-GATCCGATCXXXXGATCG-3' (SEQ ID NO:10)
3'-GCTAGXXXXCTAGCCTAG-5' (SEQ ID NO:10)

(g) Recovery of A:A complexes by ligation and amplification. In this step, new adaptors are ligated onto the ends of the A:A molecules and the molecules are amplified by PCR.

What is claimed is:

1. A method for analyzing or detecting for a target nucleic acid present in a first nucleic acid sample and not in a second nucleic acid sample comprising:
   (a) separately fragmenting nucleic acid from the first nucleic acid sample and from the second nucleic acid sample with at least one restriction endonuclease to create first nucleic acid sample fragments and second nucleic acid sample fragments respectively;
   (b) ligating a pair of first nucleic acid adaptors to the first nucleic acid fragments, each adaptor having a first restriction site and amplifying the first nucleic acid fragments with a primer complementary to the first nucleic acid adaptors and further containing a ligand binding end;
   (c) ligating a pair of second nucleic acid adaptors to the second nucleic acid fragments, each adaptor having a second restriction site different from the first restriction site and amplifying the second nucleic acid fragments with a primer complementary to the second nucleic acid sample adaptors and further containing a ligand binding end; then
   (d) combining the first nucleic acid fragments and the second nucleic acid fragments under hybridization conditions; and
   (e) isolating double-stranded nucleic acid in which both strands are first nucleic acid fragments which are representative of nucleic acid in the first nucleic acid sample not present in the second nucleic acid sample.

2. The method of claim 1, further wherein the first and the second nucleic acid fragments are subjected to a restriction endonuclease specific for the first restriction site after step (d) and before step (e).

3. The method of claim 2, further wherein the double-stranded first nucleic acid of step (e) is isolated by physical capture.

4. The method of claim 1, further wherein the first and the second nucleic acid samples are fragmented using a staggered cutting restriction endonuclease in step (a) and the end of the first nucleic acid adaptors to be ligated to the fragments comprises a nucleic acid sequence complementary to a staggered end created by the restriction endonuclease.

5. The method of claim 1, further wherein the ligand binding end of the first nucleic acid adaptors or the second nucleic acid adaptors is biotin.

6. The method of claim 5, further wherein the first and the second nucleic acid fragments are subjected to a restriction endonuclease specific for the first restriction site after step (d) and before step (e), and then the double-stranded first nucleic acid of step (e) is isolated by passing the first and the second nucleic acid fragments through a streptavidin column.

7. The method of claim 1, further wherein the first and the second nucleic acid samples are fragmented using a staggered cutting restriction endonuclease in step (a) and the end of the second nucleic acid adaptors to be ligated to the fragments comprises a nucleic acid sequence complementary to a staggered end created by the restriction endonuclease.

8. A method for analyzing or detecting for a target nucleic acid present in a first nucleic acid sample and not in a second nucleic acid sample comprising:
   (a) separately fragmenting nucleic acid from the first nucleic acid sample and from the second nucleic acid sample with at least one restriction endonuclease to create first nucleic acid fragments and second nucleic acid fragments respectively;
   (b) ligating a pair of first nucleic acid adaptors to the first nucleic acid fragments, each adaptor having a first restriction site and a ligand binding end;
   (c) ligating a pair of second nucleic acid adaptors to the second nucleic acid fragments, each adaptor having a second restriction site different from the first restriction site and a ligand binding end; then
   (d) combining the first nucleic acid fragments and the second nucleic acid fragments under hybridization conditions; and (e) isolating double-stranded nucleic acid in which both strands are first nucleic acid fragments which are representative of nucleic acid in the first nucleic acid sample and not in the second nucleic acid sample.

9. The method of claim 8, further wherein the first and the second nucleic acid fragments are subjected to a restriction endonuclease specific for the first restriction site after step (d) and before step (e).

10. The method of claim 9, further wherein the double-stranded first nucleic acid of step (e) is isolated by physical capture.

11. The method of claim 8, further wherein the first and the second nucleic acid samples are fragmented using a staggered cutting restriction endonuclease in step (a) and the end of the first nucleic acid adaptors to be ligated to the fragments comprises a nucleic acid sequence complementary to a staggered end created by the restriction endonuclease.

12. The method of claim 8, further wherein the ligand binding end of the first nucleic acid adaptors or the second nucleic acid adaptors is biotin.

13. The method of claim 12, further wherein the first and the second nucleic acid fragments are subjected to a restriction endonuclease specific for the first restriction site after step (d) and before step (e), and then the double-stranded first nucleic acid of step (e) is isolated by passing the first and the second nucleic acid fragments through a streptavidin column.

14. The method of claim 8, further wherein the first and the second nucleic acid samples are fragmented using a staggered cutting restriction endonuclease in step (a) and the end of the second nucleic acid adaptors to be ligated to the fragments comprises a nucleic acid sequence complementary to a staggered end created by the restriction endonuclease.

15. The method of claim 1, further wherein an additional step (f) is included, said step comprising separating strands of the double-stranded first nucleic acid in step (e).

16. The method of claim 1, further wherein an additional step (f) is included, said step comprising sequencing at least one of the first nucleic acid fragments of step (e).

* * * * *

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: DNA ( i x ) FEATURE:
        ( A ) NAME/KEY: modified_base
        ( B ) LOCATION: 1
        ( D ) OTHER INFORMATION: /mod_base=OTHER
            / note= "N = any biotinylated nucleotide"

( i x ) FEATURE:
        ( A ) NAME/KEY: misc_feature
        ( B ) LOCATION: 1..30
        ( D ) OTHER INFORMATION: /note= "complementary strand to
            SEQ ID NO:2"

( x i ) SEQUENCE DESCRIPTION: SEQ ID NO:1:

NNNGGATCCG ATCTTTTGAT CGGATCCNNN                30

( 2 ) INFORMATION FOR SEQ ID NO:2:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: DNA ( i x ) FEATURE:
        ( A ) NAME/KEY: modified_base
        ( B ) LOCATION: 1
        ( D ) OTHER INFORMATION: /mod_base=OTHER
            / note= "N = any biotinylated nucleotide"

( i x ) FEATURE:
        ( A ) NAME/KEY: misc_feature
        ( B ) LOCATION: 1..30
        ( D ) OTHER INFORMATION: /note= "complementary strand to
            SEQ ID NO:1"

( x i ) SEQUENCE DESCRIPTION: SEQ ID NO:2:

NNNGGATCCG ATCAAAAGAT CGGATCCNNN                30

( 2 ) INFORMATION FOR SEQ ID NO:3:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: DNA ( i x ) FEATURE:
        ( A ) NAME/KEY: modified_base
        ( B ) LOCATION: 1
        ( D ) OTHER INFORMATION: /mod_base=OTHER
            / note= "N = any biotinylated nucleotide"

( i x ) FEATURE:
        ( A ) NAME/KEY: misc_feature ( B ) LOCATION: 1..30
( D ) OTHER INFORMATION: /note= "complementary strand to SEQ ID NO:4"

( x i ) SEQUENCE DESCRIPTION: SEQ ID NO:3:

NNNGGATCCG ATCGGGGGAT CGGATCCNNN    30

( 2 ) INFORMATION FOR SEQ ID NO:4:

( i ) SEQUENCE CHARACTERISTICS:
      ( A ) LENGTH: 30 base pairs
      ( B ) TYPE: nucleic acid
      ( C ) STRANDEDNESS: double
      ( D ) TOPOLOGY: linear ( i i ) MOLECULE TYPE: DNA ( i x ) FEATURE:
      ( A ) NAME/KEY: modified_base
      ( B ) LOCATION: 1
      ( D ) OTHER INFORMATION: /mod_base=OTHER
        / note= "N = any biotinylated nucleotide"

( i x ) FEATURE:
      ( A ) NAME/KEY: misc_feature
      ( B ) LOCATION: 1..30
      ( D ) OTHER INFORMATION: /note= "complementary strand to SEQ ID NO:3"

( x i ) SEQUENCE DESCRIPTION: SEQ ID NO:4:

NNNGGATCCG ATCCCCCGAT CGGATCCNNN    30

( 2 ) INFORMATION FOR SEQ ID NO:5:

( i ) SEQUENCE CHARACTERISTICS:
      ( A ) LENGTH: 30 base pairs
      ( B ) TYPE: nucleic acid
      ( C ) STRANDEDNESS: double
      ( D ) TOPOLOGY: linear ( i i ) MOLECULE TYPE: DNA ( i x ) FEATURE:
      ( A ) NAME/KEY: modified_base
      ( B ) LOCATION: 1
      ( D ) OTHER INFORMATION: /mod_base=OTHER
        / note= "N = any biotinylated nucleotide"

( i x ) FEATURE:
      ( A ) NAME/KEY: misc_feature
      ( B ) LOCATION: 1..30
      ( D ) OTHER INFORMATION: /note= "sequence is complementary to itself"

( x i ) SEQUENCE DESCRIPTION: SEQ ID NO:5:

NNNGGATCCG ATCNNNNGAT CGGATCCNNN    30

( 2 ) INFORMATION FOR SEQ ID NO:6:

( i ) SEQUENCE CHARACTERISTICS:
      ( A ) LENGTH: 30 base pairs
      ( B ) TYPE: nucleic acid
      ( C ) STRANDEDNESS: double
      ( D ) TOPOLOGY: linear ( i i ) MOLECULE TYPE: DNA ( i x ) FEATURE:
      ( A ) NAME/KEY: modified_base
      ( B ) LOCATION: 1
      ( D ) OTHER INFORMATION: /mod_base=OTHER
        / note= "N = any biotinylated nucleotide"

( i x ) FEATURE:

(A) NAME/KEY: misc_feature
(B) LOCATION: 1..30
(D) OTHER INFORMATION: /note= "complementary strand to SEQ ID NO:7"

(xi) SEQUENCE DESCRIPTION: SEQ ID NO:6:

NNNAGATCTG ATCTTTTGAT CAGATCTNNN        30

(2) INFORMATION FOR SEQ ID NO:7:

(i) SEQUENCE CHARACTERISTICS:
(A) LENGTH: 30 base pairs
(B) TYPE: nucleic acid
(C) STRANDEDNESS: double
(D) TOPOLOGY: linear (ii) MOLECULE TYPE: DNA (ix) FEATURE:
(A) NAME/KEY: modified_base
(B) LOCATION: 1
(D) OTHER INFORMATION: /mod_base=OTHER
/ note= "N = any biotinylated nucleotide"

(ix) FEATURE:
(A) NAME/KEY: misc_feature
(B) LOCATION: 1..30
(D) OTHER INFORMATION: /note= "complementary strand to SEQ ID NO:6"

(xi) SEQUENCE DESCRIPTION: SEQ ID NO:7:

NNNAGATCTG ATCAAAAGAT CAGATCTNNN        30

(2) INFORMATION FOR SEQ ID NO:8:

(i) SEQUENCE CHARACTERISTICS:
(A) LENGTH: 30 base pairs
(B) TYPE: nucleic acid
(C) STRANDEDNESS: double
(D) TOPOLOGY: linear (ii) MOLECULE TYPE: DNA (ix) FEATURE:
(A) NAME/KEY: modified_base
(B) LOCATION: 1
(D) OTHER INFORMATION: /mod_base=OTHER
/ note= "N = any biotinylated nucleotide"

(ix) FEATURE:
(A) NAME/KEY: misc_feature
(B) LOCATION: 1..30
(D) OTHER INFORMATION: /note= "complementary strand to SEQ ID NO:9"

(xi) SEQUENCE DESCRIPTION: SEQ ID NO:8:

NNNAGATCTG ATCGGGGGAT CAGATCTNNN        30

(2) INFORMATION FOR SEQ ID NO:9:

(i) SEQUENCE CHARACTERISTICS:
(A) LENGTH: 30 base pairs
(B) TYPE: nucleic acid
(C) STRANDEDNESS: double
(D) TOPOLOGY: linear (ii) MOLECULE TYPE: DNA (ix) FEATURE:
(A) NAME/KEY: modified_base
(B) LOCATION: 1
(D) OTHER INFORMATION: /mod_base=OTHER
/ note= "N = any biotinylated nucleotide"

(i x) FEATURE:
    (A) NAME/KEY: misc_feature
    (B) LOCATION: 1..30
    (D) OTHER INFORMATION: /note= "complementary strand to SEQ ID NO:8"

(x i) SEQUENCE DESCRIPTION: SEQ ID NO:9:

NNNAGATCTG ATCCCCGAT CAGATCTNNN                     30

(2) INFORMATION FOR SEQ ID NO:10:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (i i) MOLECULE TYPE: DNA (i x) FEATURE:
        (A) NAME/KEY: misc_feature
        (B) LOCATION: 1..18
        (D) OTHER INFORMATION: /note= "sequence is complementary to itself"

(x i) SEQUENCE DESCRIPTION: SEQ ID NO:10:

GATCCGATCN NNNGATCG                                 18